US00PP25663P2

(12) United States Plant Patent
Hansen

(10) Patent No.: US PP25,663 P2
(45) Date of Patent: Jun. 30, 2015

(54) ***BAPTISIA* PLANT NAMED 'VANILLA CREAM'**

(50) Latin Name: ***Baptisia* hybrid**
Varietal Denomination: Vanilla Cream

(71) Applicant: Hans Andrew Hansen, Zeeland, MI (US)

(72) Inventor: Hans Andrew Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 183 days.

(21) Appl. No.: 13/987,470

(22) Filed: Jul. 29, 2013

(51) Int. Cl.
*A01H 5/02* (2006.01)

(52) U.S. Cl.
USPC ..... Plt./263.1

(58) Field of Classification Search
USPC ..... Plt./263.1, 226
See application file for complete search history.

*Primary Examiner* — June Hwu
(74) *Attorney, Agent, or Firm* — Penny J. Aguirre

(57) ABSTRACT

A new cultivar of interspecific *Baptisia*, 'Vanilla Cream', that is characterized by its creamy white flowers held on erect flower stems, with growth tips that are brown-purple in color, its densely branched, uniform and compact plant habit, its moderate growth rate, and its hardiness in U.S.D.A. Zones 4 to 8.

2 Drawing Sheets

Botanical classification: *Baptisia* hybrid.

Cultivar designation: 'Vanilla Cream'.

The present invention relates to a new and distinct cultivar of *Baptisia* plant of hybrid origin, botanically known as *Baptisia* 'Vanilla Cream' and will be referred to hereafter by its cultivar name, 'Vanilla Cream'. The new cultivar represents a new false indigo, an herbaceous perennial grown for landscape use.

The new Invention arose from an ongoing controlled breeding program in Waseca, Minn. that was established by the Inventor in 1998 using superior selections of numerous species of *Baptisia* with the goal of developing unique color forms and plant habits of *Baptisia* suited for general garden and landscape use.

'Vanilla Cream' was derived from seed collected after open pollination of many unnamed plants of different species of *Baptisia* in a trial bed in 1998. 'Vanilla Cream' was selected in 2007 as a single plant amongst the resulting seedlings. Based on the characteristics of the new cultivar, the parent plants are believed to be *Baptisia cinera* and *Baptisia alba.*

Asexual propagation of the new cultivar was first accomplished by stem cuttings in 2008 in Zeeland, Mich. under the direction of the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Vanilla Cream' as a unique cultivar of *Baptisia.*

1. 'Vanilla Cream' exhibits flowers that are creamy white in color.
2. 'Vanilla Cream' exhibits blue-green foliage.
3. 'Vanilla Cream' exhibits new growth tips that are brown-purple in color.

4. 'Vanilla Cream' exhibits a compact, mounded growth habit.
5. 'Vanilla Cream' is hardy in U.S.D.A. Zones 4 to 8.

'Vanilla Cream' differs from the parent plant *Baptisia cinera* in having flowers that are creamy white in color rather than yellow. In addition, the inflorescences of 'Vanilla Cream' are significantly longer and held upright compared to the shorter flower spikes of *B. cinera,* which are held at a 45° angle. 'Vanilla Cream' can also be compared to *B. albescens* and *B. alba.* 'Vanilla Cream' is similar to both in flowering habit, but differs by having a more compact growth habit and a more mounding form rather than the vase-shaped growth habit of *B. alba* and *B. albescens*. 'Vanilla Cream' can also be compared to *B. leucophaea*. 'Vanilla Cream' differs from *B. leucophaea* in having upright inflorescence rather than horizontal, a larger growth habit, leaves that are not pubescent, and having flowers that are whiter in color.

BRIEF DESCRIPTION OF THE DRAWING

The accompanying colored photographs illustrate the overall appearance and distinct characteristics of the new *Baptisia*. The photographs were taken of a plant about seven years in age as grown outdoors in a garden in Zeeland, Mich.

The photograph in FIG. 1 is a view of a plant of 'Vanilla Cream' in bloom and illustrates the dense, uniform habit and the abundance of flower stems.

Figure 1:
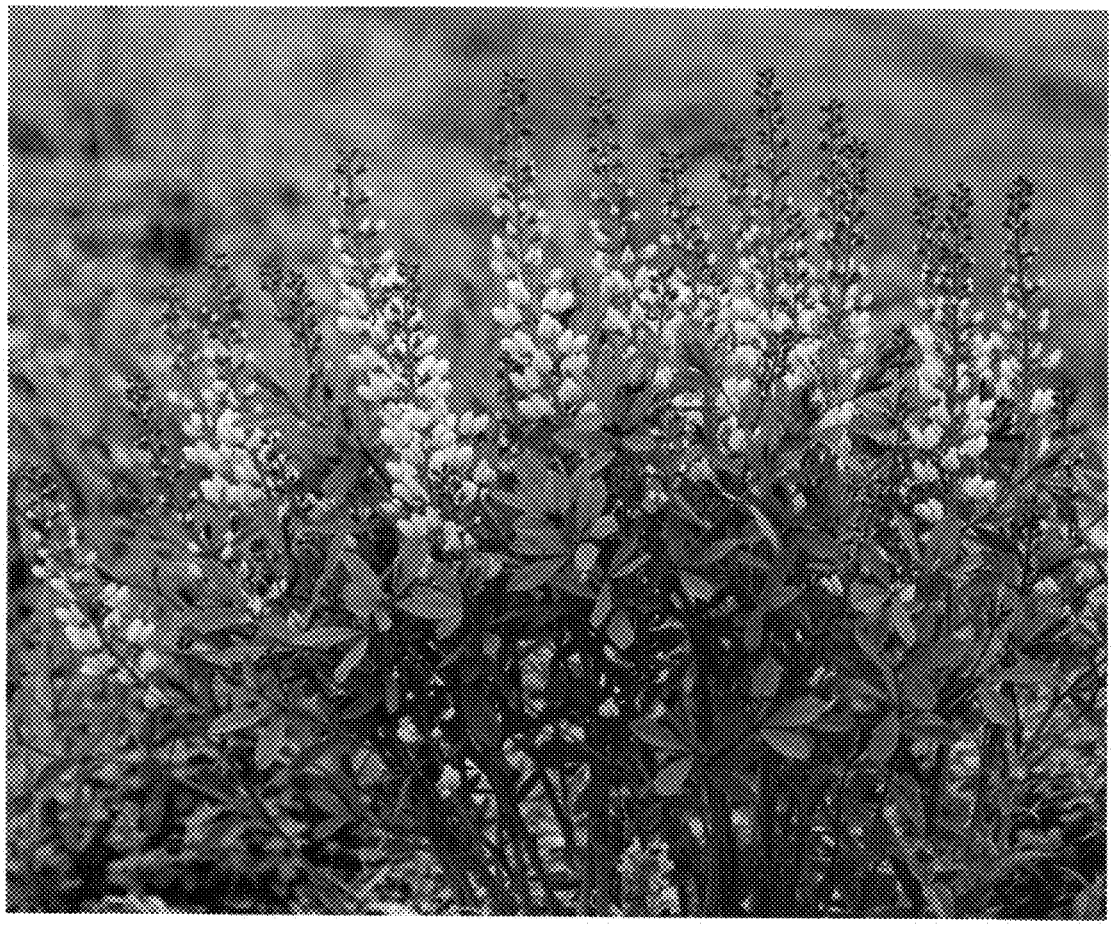
Figure 2:
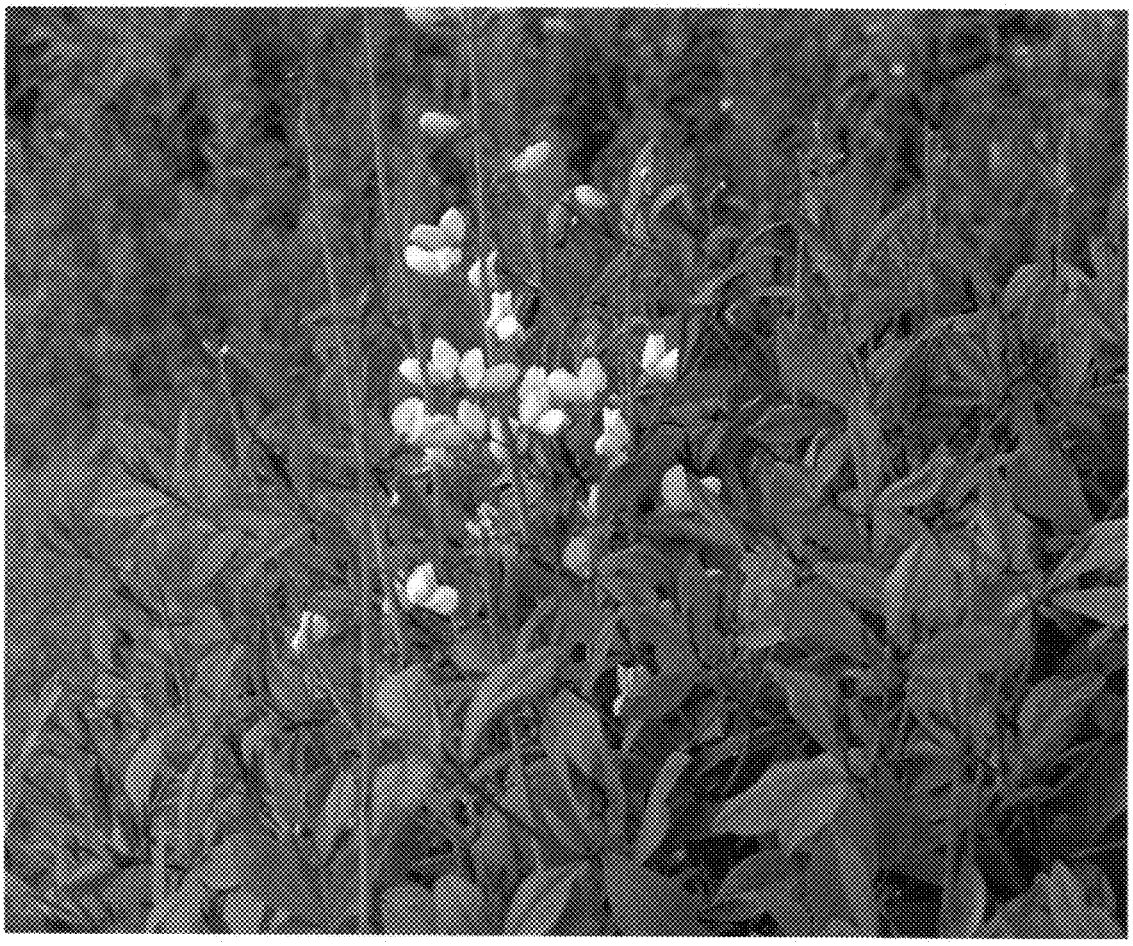

The photograph in FIG. 2 provides a view of the new growth tips of 'Vanilla Cream'.

The colors in the photographs may differ slightly from the color values cited in the detailed botanical description, which accurately describe the colors of the new *Baptisia.*

DETAILED BOTANICAL DESCRIPTION OF THE PLANT

The following is a detailed description of 5 year-old plants of the new cultivar as grown outdoors in a trial plot in Waseca, Minn. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period.*—Early June through late June in Waseca, Minn. (June 5$^{th}$-June 25$^{th}$).

*Plant habit.*—Upright with a dense, spreading mound of foliage on upper portion of plant.

*Height and spread.*—Reaches 78 cm width and 53 cm in height.

*Hardiness.*—U.S.D.A. Zones 4 to 8.

*Culture.*—Prefers well-drained to medium moist soils in full sun, tolerant to lean soils and drought.

*Diseases and pests.*—No susceptibility to diseases or pests has been observed.

*Root description.*—Deep rooted, fibrous.

Growth and propagation:

*Propagation.*—Stem cuttings, tissue culture is also possible.

*Growth rate.*—Moderate.

Stem description:

*Branch habit.*—Densely branched; average of 23 branches with an average of 3 secondary branches, and 2 tertiary branches.

*Stem size.*—Main stem; average of 70 cm (including peduncle) in length and 5 mm in width, secondary; average of 28 cm in length and 4 mm, tertiary; an average of 5.2 cm in length and 2 mm in width.

*Stem shape.*—Oval.

*Stem color.*—144A.

*Stem surface.*—Hairless, satiny but slightly glaucous with ridges.

Foliage description:

*Leaf shape.*—Fan-shaped in overall outline.

*Leaf division.*—3-palmate.

*Leaf internode.*—Foliage begins 22 cm from base, an average of 6.5 cm on main stem and an average of 3 cm on secondary branches.

*Leaf size.*—Average 6 cm in length and 8 cm in width when mature.

*Leaf quantity.*—About 21 per stem.

*Leaflet shape.*—Oblanceolate.

*Leaflet base.*—Cuneate.

*Leaflet apex.*—Acute.

*Leaflet venation.*—Pinnate pattern, not conspicuous, color matches leaflet color on the upper and lower surface with the mid rib of lower surface 197A.

*Leaflet margins.*—Entire.

*Leaf attachment.*—Petiolate.

*Leaf arrangement.*—Alternate.

*Leaflet surface.*—Glabrous and slightly glaucous on upper and lower surface.

*Leaflet color.*—New growth; upper and lower surface; a blend of N77A and 166A, maturing; upper and lower surface 137B, mature; upper and lower surface 138A.

*Leaflet size.*—An average of 5 cm in length and 1.5 cm in width.

*Petioles.*—Average of 7 mm in length and 2 mm in width, clasping to stem at mature nodes, 147C in color, surface is glabrous and satiny.

*Stipules.*—Lanceolate in shape, base is truncate to stem, apex is narrowly acute to acuminate, up to 2.4 cm in length and 8 mm in width on mature leaves, 137B in color on upper and lower surface.

Flower description:

*Inflorescence type.*—Terminal racemes of pea-like flowers on main and secondary branches, blooms from the base to the apex.

*Inflorescence size.*—Average of 27.5 cm in length and 3 cm in width in mid section.

*Lastingness of inflorescence.*—About 20 days.

*Flower size.*—About 2.5 cm in depth and about 1.5 cm in diameter.

*Flower fragrance* .—Faint.

*Flower number per inflorescence.*—About 32 to 40.

*Peduncle.*—Oval in shape, up to 30 cm in length and an average of 4 mm in width, 137B in color, surface is glabrous, satiny and slightly glaucous with ridges, flower internode length averages 2 cm.

*Petiole.*—About 7 mm in length, about 1 mm in width, oval in shape, N186B, glabrous and satiny surface.

*Flower buds.*—Kidney-shaped, about 2.8 cm in length and 1 cm in width, petal portion is 4C in color, calyx portion same as open flowers.

*Flower type.*—Papilionaceous, held at about a 45° angle.

*Calyx.*—Campanulate, about 1 cm in length and 6 mm in diameter, surface is glabrous and satiny, blend of 144A and 144B, persistent.

*Sepals.*—5, fused with the exception of apex of each, free portion is triangular in shape 4 mm in width and 4 mm in depth with an acute apex, blend of 144A and 144B.

*Corolla features.*—Papilionaceous (4 segments) with a reflexed banner, 2 lateral and a concealed keel, lateral wings; oblong in shape, about 2 cm in length and 8 mm in width, color on outer surface and the inner surface is 4D, rounded apex, oblique base keel; not visible visible, comprised of 2 segments surrounding reproductive organs, oblong (slightly oblique) in shape with rounded apex and oblique base, 2 cm in length and 8 mm in width, upper surface and lower surface are 4D in color, segments joined at center point, banner; orbicular and strongly reflexed in shape, about 2 cm in length and 1 cm in width, upper and lower surface 4D with mid region having a base of 145B and marking of 186C, apex is rounded with a single notch, surface is glabrous on all sections.

*Receptacle.*—Disk-shaped, gelatinous, 144A in color, about 3.5 mm in diameter and 1.5 mm in depth.

Reproductive organs:

*Gynoecium.*—1 Pistil, about 2.3 cm in length, 1.5 mm in width; style is N144B in color and 8 mm in length; stigma minute, too small to read color, ovary is superior with a stipe, N144A in color, 1 cm in length and 2 mm in width; stipe is N144B in color, 4 mm in length and 1.5 mm in width.

*Androcoecium.*—10 stamens, not united, 2.5 cm in length and 1 mm in width; filament is 1.8 cm in length, 1 mm in width and 160C in color; anther is dorsifixed, 2 mm in length and 1 mm in width and 165B in color, pollen is moderate in quantity and N163D in color.

*Fruit and seed.*—An inflated pod, technically a legume, 32 to 40 produced per inflorescence (open-pollinated), globose-oblongoid in shape, about 42 mm in length by 15 to 20 mm in width; each with a short beak approx. 7 mm in length, emerges 144A and matures in September to 200A in color, interior color between 199B and 199C, glossy, walls thin, 0.5 mm, seed; 12 to 22 per fruit (open-pollinated), 165B in color, oval with the hilum side more or less straight, seed compressed to flattish, 4 mm in length, 3 mm in width and 1.5 mm in thickness.

It is claimed:

1. A new and distinct cultivar of *Baptisia* plant named 'Vanilla Cream' as herein illustrated and described.

* * * * *